United States Patent [19]

Winston et al.

[11] Patent Number: 5,833,957
[45] Date of Patent: Nov. 10, 1998

[54] PROCESSES AND COMPOSITIONS FOR THE REMINERALIZATION OF TEETH

[75] Inventors: Anthony E. Winston, East Brunswick; Norman Usen, Marlboro, both of N.J.

[73] Assignee: Enamelon, Inc., East Brunswick, N.J.

[21] Appl. No.: 917,885

[22] Filed: Aug. 27, 1997

Related U.S. Application Data

[60] Continuation of Ser. No. 722,459, Sep. 27, 1996, abandoned, which is a division of Ser. No. 512,473, Aug. 8, 1995, Pat. No. 5,603,922.

[51] Int. Cl.$^6$ ............................................. A61K 7/16
[52] U.S. Cl. ............................. 424/49; 424/52; 424/57
[58] Field of Search ............................ 424/49, 52, 57

[56] References Cited

U.S. PATENT DOCUMENTS

| | | | |
|---|---|---|---|
| 1,698,404 | 1/1929 | Hopkins . | |
| 2,605,229 | 7/1952 | Marcus | 252/317 |
| 2,627,493 | 2/1953 | Merckel et al. | 167/93 |
| 2,700,012 | 1/1955 | Merckel et al. | 167/93 |
| 3,679,360 | 7/1972 | Rubin | 23/109 |
| 3,728,446 | 4/1973 | Roberts et al. | 424/49 |
| 3,747,804 | 7/1973 | Raaf et al. | 222/1 |
| 3,913,229 | 10/1975 | Driskell et al. | 32/15 |
| 3,943,267 | 3/1976 | Randol | 427/2 |
| 3,966,901 | 6/1976 | Cullum et al. | 424/52 |
| 4,048,300 | 9/1977 | Tomlinson et al. | 424/52 |
| 4,075,317 | 2/1978 | Mitchell et al. | 424/52 |
| 4,080,440 | 3/1978 | DiGiulio | 424/49 |
| 4,083,955 | 4/1978 | Grabenstetter et al. | 424/49 |
| 4,097,588 | 6/1978 | Levine | 424/52 |
| 4,097,935 | 7/1978 | Jarcho | 3/1.9 |
| 4,108,980 | 8/1978 | Duff | 424/52 |
| 4,138,477 | 2/1979 | Gaffar | 424/52 |
| 4,141,969 | 2/1979 | Mitchell | 424/52 |
| 4,150,112 | 4/1979 | Wagenknecht et al. | 424/48 |
| 4,159,315 | 6/1979 | Wagenknecht et al. | 424/48 |
| 4,177,258 | 12/1979 | Gaffar et al. | 424/52 |
| 4,183,915 | 1/1980 | Gaffar et al. | 424/52 |
| 4,233,288 | 11/1980 | Cornell | 424/48 |
| 4,244,707 | 1/1981 | Wason | 51/308 |
| 4,265,877 | 5/1981 | Tenta | 424/48 |
| 4,280,822 | 7/1981 | Wason | 51/308 |
| 4,283,385 | 8/1981 | Dhabbar et al. | 424/52 |
| 4,340,584 | 7/1982 | Wason | 424/52 |
| 4,348,381 | 9/1982 | Gaffar et al. | 424/52 |
| 4,397,837 | 8/1983 | Raaf et al. | 424/51 |
| 4,405,600 | 9/1983 | Besic | 424/57 |
| 4,412,983 | 11/1983 | Mitchell | 424/52 |
| 4,415,550 | 11/1983 | Pakhomov et al. | 424/52 |
| 4,419,341 | 12/1983 | Kokesnik et al. | 424/52 |
| 4,424,203 | 1/1984 | Pakhomov et al. | 424/52 |
| 4,460,565 | 7/1984 | Weststrate et al. | 424/52 |
| 4,474,749 | 10/1984 | Kruppa | 424/48 |
| 4,487,757 | 12/1984 | Kiozpeoplou | 424/49 |
| 4,515,770 | 5/1985 | Besic | 424/49 |
| 4,518,430 | 5/1985 | Brown et al. | 106/35 |
| 4,528,180 | 7/1985 | Schaeffer | 424/52 |
| 4,532,124 | 7/1985 | Pearce | 424/52 |
| 4,556,561 | 12/1985 | Brown et al. | 424/151 |
| 4,565,691 | 1/1986 | Jackson | 42/52 |
| 4,603,045 | 7/1986 | Smigel | 424/52 |
| 4,606,912 | 8/1986 | Rudy et al. | 424/52 |
| 4,610,873 | 9/1986 | Rudy et al. | 424/52 |
| 4,612,053 | 9/1986 | Brown et al. | 706/35 |
| 4,672,032 | 6/1987 | Slavkin et al. | 435/68 |
| 4,714,608 | 12/1987 | Rolla | 424/52 |
| 4,812,306 | 3/1989 | Cockerell et al. | 424/52 |
| 4,824,681 | 4/1989 | Schobel et al. | 426/5 |
| 4,828,823 | 5/1989 | Li | 424/52 |
| 4,837,007 | 6/1989 | Duckworth et al. | 424/52 |
| 4,931,272 | 6/1990 | Dany et al. | 424/49 |
| 4,980,154 | 12/1990 | Gordon | 424/53 |
| 4,983,379 | 1/1991 | Schaeffer | 424/52 |
| 5,037,639 | 8/1991 | Tung | 424/57 |
| 5,041,280 | 8/1991 | Smigel | 424/52 |
| 5,045,305 | 9/1991 | Clarkson et al. | 424/52 |
| 5,047,031 | 9/1991 | Constantz | 606/77 |
| 5,124,160 | 6/1992 | Zibell et al. | 426/3 |
| 5,129,905 | 7/1992 | Constantz | 606/76 |
| 5,139,769 | 8/1992 | Gaffar et al. | 424/52 |
| 5,145,668 | 9/1992 | Chow et al. | 424/52 |
| 5,268,167 | 12/1993 | Tung | 424/52 |
| 5,378,131 | 1/1995 | Greenberg | 424/440 |
| 5,427,768 | 6/1995 | Tung | 424/52 |
| 5,437,857 | 8/1995 | Tung | 424/52 |
| 5,460,803 | 10/1995 | Tung | 424/57 |
| 5,476,647 | 12/1995 | Chow et al. | 424/52 |

OTHER PUBLICATIONS

J. Dent Res., vol. 76, Special Issue, p. 134 Abstract 965.
J. Dent Res., vol. 76, Special Issue, p. 255 Abstract 1931.
J. Dent Res., vol. 76, Special Issue, p. 376 Abstract 2897.
International Application Publication WO94/18938, Sep. 1, 1994.

*Primary Examiner*—Hoa Van Le
*Attorney, Agent, or Firm*—Depaoli & Frenkel, P.C.

[57] ABSTRACT

The present invention relates to remineralization, without demineralization, by applying to the teeth a composition which is present in either one or in two phases and which does not react to any large extent until introduced into the oral cavity and upon such introduction does not rapidly precipitate. One phase systems contain at least one water-soluble calcium compound, at least one other water-soluble, non-toxic compound containing a divalent metal different from calcium, and at least one water-soluble inorganic phosphate compound. If desired at least one water-soluble fluorine compound may be added to the system. In two phase systems one phase contains the calcium and the divalent metal compounds and the other the phosphate and optionally, the fluoride compound. In this way the ions which effect remineralization can be absorbed by the dental enamel and their subsequent, but controlled, reaction causes rehardening of demineralized areas in the dental enamel.

16 Claims, No Drawings

PROCESSES AND COMPOSITIONS FOR THE REMINERALIZATION OF TEETH

This application is a continuation of application Ser. No. 08/722,459, filed Sep. 27, 1996, now abandoned, which is a division of application Ser. No. 512,473, filed Aug. 8, 1995, U.S. Pat. No. 5,603,922.

BACKGROUND OF THE INVENTION

1. Field of the Invention

This invention relates to processes and compositions which are useful to more effectively remineralize subsurface lesions in teeth. More specifically, this invention relates to soluble salt, compositions such as soluble calcium salts and phosphate salts, which are applied to lesions in dental enamel resulting in remineralization of subsurface dental enamel and/or mineralizing tubules in dentin thereby counteracting caries and/or hypersensitivity. The soluble salts may be contained in toothpastes, gels, mouthwashes, wafers, lozenges, chewing gum, and the like, using both single vehicle systems, e.g., a stable dry blend or a stable solution, or two vehicle system, e.g., two dry salts separated by a barrier or two solutions wherein one contains calcium ions and the other phosphate ions.

2. The Prior Art

The primary component of the enamel and dentin in teeth is calcium phosphate in the form of calcium hydroxyapatite. This material is highly insoluble at normal oral pHs. However, carious lesions form in teeth, when they are subjected to acids produced from the glycolysis of sugars by the action of various oral bacteria. This is because calcium phosphate salts are more soluble in acidic media.

Saliva is supersaturated with respect to calcium and phosphate ions. Saliva therefore helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva the addition of higher levels of dissolved calcium and phosphate ions is not easily accomplished.

Remineralization of dental enamel has been carried out experimentally both in vivo and in vitro. Some studies have concentrated on the remineralizing properties of saliva and synthetic solutions supersaturated with respect of hydroxyapatite. Such studies comprise the subject matter of U.S. Pat. Nos. 3,679,360 (Rubin) and 4,097,935 (Jarcho).

Generally, the supersaturated solutions or slurries used in these patents for remineralization experiments have been prepared from a single form of calcium phosphate. When a carious lesion is flooded with one of these supersaturated solutions, the calcium and phosphate ions in the form of precipitated hydroxyapatite remineralize the lesion.

However, these solutions are impractical for use for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and damage the dental tissue.

U.S. Pat. No. 4,080,440 (Digiulio et al) discloses a metastable solution of calcium and phosphate ions at a low pH (between 2.5 to 4.0) under which conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et al) provide for a remineralizing solution containing supersaturated concentrations of calcium ions, phosphate ions and a fluoride source stabilized by the presence of an antinucleating agent such as diamine tetramethylene-phosphonic acid, ethylenediamine tetramethylenephosphonic acid and 2-phosphonobutane-tricarboxylic acid-1,2,4, or the water-soluble salts thereof. This solution is preferably adjusted to the neutral pH range where it is alleged to most effectively remineralize sub-surface lesions. Even though the antinucleating agent would be expected to stabilize the solution, equilibrium of the supersaturated concentrations is still found difficult to maintain and avoid precipitation of hydroxyapatite and changes in the pH of the solution.

U.S. Pat. Nos. 4,083,955 (Grabenstetter et al) and 4,397,837 (Raaf et al) provide a process for remineralizing demineralized enamel by the consecutive treatment of tooth surfaces with separate solutions containing calcium ions and phosphate ions. In this process fluoride ions may be present in the phosphate solutions. It is immaterial which ionic solution is used to treat the teeth first. By sequentially applying calcium and phosphate ions to the tooth surface high concentrations of the ions are able to penetrate into lesions in solution form, where they precipitate as a calcium phosphate salt when ions from the second treatment solution diffuse in. While apparently successful this method involves the inconvenience of a plurality of sequential applications which can also be found to be time consuming.

U.S. Pat. No. 4,606,912 (Rudy et al) provides a method of making a clear aqueous mouthwash solution capable of remineralizing lesions in teeth by forming an aqueous solution containing a source of calcium ions and a chelating agent for calcium ions, causing the chelation of at least 50% of the calcium ions and subsequently adding a source of phosphate ions to the aqueous solution. Here too while somewhat effective, the addition and necessary control of the amount of chelating agent makes the concept impractical.

Another problem with known remineralization techniques is that the remineralization may stop before the lesion is completely remineralized due to build up of the remineralized tooth material in or on the outer layer of the tooth's surface. This build up occurs when the rate of remineralization is too fast and prevents the diffusion of the mineral into the deeper regions of the lesion, thus thwarting the full remineralization of the tooth.

There is a need for a method of remineralizing dental enamel that does not require excessive amounts of solution and inordinately long or frequent exposure times.

It is the object of the present invention to provide a process and especially a composition for the remineralization and the prevention of demineralization of human teeth, which process and composition are capable of effectively incorporating calcium ions, phosphate ions, and if desired, fluoride ions into the dental enamel, the composition also being easily usable by the consumer and not differing significantly, in flavor and appearance, from customary dental cosmetics.

It is another object of this invention to provide an improved composition and a method of preparing said composition which is maintainable in a single container, substrate or matrix and which is capable of remineralizing lesions in the teeth and mineralizing normal teeth to prevent cariogenic lesions from forming.

SUMMARY OF THE INVENTION

In accordance with the present invention the problems of remineralization, without demineralization are solved by applying to the teeth a composition which is present in either one or in two phases which do not react to any large extent until introduced into the oral cavity and upon introduction do not rapidly precipitate. One phase systems contain at least one water-soluble calcium compound, at least one other water-soluble, non-toxic compound containing a divalent metal different from calcium, and at least one water-soluble inorganic phosphate compound. If desired at least one water-soluble fluorine compound may be added to the system. In two phase systems one phase contains the calcium and the divalent metal compound and the other the phosphate and optionally, the fluoride compound. In this way the ions which effect remineralization can be absorbed by the dental enamel and their subsequent, but controlled, reaction causes rehardening of demineralized areas in the dental enamel.

It has been found that effective remineralizing treatments can be prepared by directly combining solutions or preparations of soluble salts containing high concentrations of calcium, phosphate and, if desired, fluoride ions and applying them to teeth at moderate pHs. However, the calcium must be prevented from reaction with the phosphate ions or fluoride ions until immediately before use and preferably prevented from rapidly precipitating so as to allow ample time for diffusion of calcium and phosphate ions into the teeth. This can be accomplished by utilizing, in addition to the calcium compound, at least one other water-soluble, non-toxic divalent metal salt. The divalent metal is preferably a metal selected from the group consisting of magnesium, strontium, tin, and zinc. Magnesium is the most preferred divalent metal.

It is an advantage of the present invention that the one-part remineralization composition can be packaged or otherwise contained as a stable dry-mix which can be subsequently suspended or dissolved in water to form a paste product or the like or a mouthwash respectively. Such dry-mix contains from about 1.0% to 80.0% of at least one calcium salt, from about 1.0% to 80.0% of at least one phosphate salt, from about 0.1% to 20.0% of at least one water-soluble divalent metal salt, wherein the metal is other than calcium, from about 0.1% to 20.0% of flavor, from about 0.1% to 30.0% of sweetener, from 0 to about 10.0% of a fluoride salt, and from 0 to about 5.0% of surfactant. The flavor is preferably provided as a spray dried powder.

It is another advantage of the present invention that one-part stable remineralizing compositions may be suitably prepared as toothpastes, gels, professional gels, i.e., those which are applied professionally or are obtained by a prescription, mouthwashes, chewing gums, lozenges, and the like.

It is still another advantage that such compositions may be made effervescent when added to water by including therein a non-toxic organic acid, e.g., malic acid and an alkali-metal bicarbonate, e.g., sodium bicarbonate.

A one-part remineralizing composition contains from about 0.05% to 15.0% water-soluble calcium salt, greater than about 0.001%, preferably from about 0.001% to 2.0%, water-soluble, non-toxic divalent metal salt wherein the metal is other than calcium, from about 0.05% to 15.0% water-soluble phosphate salt and optionally, from about 0.01% to 5.0% fluoride releasing agent. The single part dentifrice composition usually contains acidic or basic compounds which provide that the pH is between about 4.0 and 7.0, preferably, between about 5.0 and 5.75 when the dry mix is solublized or the final aqueous solution is prepared.

In a two-part system, part I contains from about 0.05% to about 15.0% water-soluble calcium salt and greater than about 0.001%, preferably from about 0.001% to 2.0%, water-soluble, non-toxic divalent metal salt wherein the metal is other than calcium, and part II contains from about 0.05% to 15.0% water-soluble phosphate salt and, optionally, from about 0.01% to 5.0% fluoride releasing agent. Again, when the two parts are mixed the pH is adjusted so as to be between about 4.0 and 7.0, and preferably between about 5.0 and 5.75. The two parts are mixed and immediately applied to the teeth being treated.

It has been found that such combinations effect remineralization of lesions but impede the precipitation of calcium phosphate so as to improve diffusion of calcium and phosphate ions into the teeth. The fluoride containing dentifrices or mouthwashes are much more effective than conventional fluoride-containing toothpastes in remineralizing teeth while the non-fluoride compositions, such as chewing gums or non-fluoride toothpastes, lozenges or non-fluoride mouthrinses, are more or less equivalent to fluoride-containing dentifrices. The compositions of the invention give substantially improved remineralization and prevention of demineralization of human teeth as compared with prior art compositions.

The disadvantages of the prior art methods are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Further, the present invention may be conveniently practiced by the public without substantially changing their dental care habits.

DESCRIPTION OF THE INVENTION

The present invention lies in the discovery that a distinct improvement is realized when teeth are remineralized or desensitized by the application of certain soluble salts yielding ions which will react to form a desirable remineralizing or desensitizing precipitate. The improvement in the application comprises the simultaneous use of a water-soluble salt of a divalent metal compound, other than calcium, which is admixed with the reactant paste, gel or solution of soluble salts which are placed in contact with the tooth surface. In this reaction selected cations and anions diffuse through the tooth surface to its demineralized subsurface. However, the additional divalent metal cations contained in the reactant paste, gel or solution stabilize the system from rapidly precipitating the calcium cations and the phosphate anions. The remineralizing cations and anions can then diffuse through the tooth surface to the demineralized subsurface without rapidly forming the precipitate which is bound to the tooth structure. As a result, the tooth's subsurface is more effectively remineralized or desensitized when an effective amount of the divalent metal cations is utilized.

By "effective amount of remineralizing system or agent" is meant an amount when used in accordance with this invention will bring about the remineralizing of teeth having carious lesions, or the mineralizing of normal teeth to prevent caries from forming and to inhibit hypersensitivity by utilizing a toothpaste, gel, or mouthwash having the various components in the amounts set forth below.

Concentrations of the cationic calcium and anionic phosphate soluble salts are from about 0.05 to 15.0% or the limit of solubility of the salt. Excess salt can be present, if desired. Concentrations from about 0.10% to 10.0% are preferred. The concentrations of the soluble salts containing the desired remineralizing anions are essentially the same as those for the water-soluble salts containing the desired cations.

Concentrations of the soluble, non-toxic divalent metal salts (other than calcium) are greater than about 0.001%, preferably between about 0.001% to 2.0%, with concentrations of about 0.01% to 1.0% being most preferred.

Although many precipitates are within the broad scope of this invention, by depositing a precipitate less soluble than the original enamel, the remineralized subsurface can be made to be more resistant to demineralization than was the original enamel. If a fluoride ion is utilized, the remineralized enamel is more resistant to demineralization than was the original enamel. The concentration of salt containing fluoride ion in the solution may be from about 0.01% to 5.0%, but from about 0.02% to 2.0% is preferred.

In order to effect remineralization of the dental enamel, an effective amount of the desired cations and anions must be employed in the oral cavity. The amount of solution generated in the mouth must contain at least 100 ppm of desired cations and 100 ppm of desired anions and preferably contains more than 1,000 ppm of desired cations and 1,000 ppm of desired anions. The solution must contain at least 10 ppm of divalent metal ions other than calcium and, preferably contains more than 100 ppm thereof. It is preferred to provide a level of fluoride ions between about 20 ppm to 5,000 ppm in the oral cavity from the dentifrice or professionally applied or prescribed gel.

While the length of time of contact between the dissolved calcium and phosphate salts and the tooth's surface is not critical, it is necessary for the length of time to be great enough to allow diffusion of the ions through the tooth's surface to the demineralized subsurface. It is submitted that at least ten seconds is required for this diffusion and preferably it should be greater than thirty seconds and even longer if possible. The desired extended time for such diffusion is a benefit acruing from the use of the divalent metal salts of this invention.

Upon preparation with water or upon use in the oral cavity with saliva any solution should have a pH of from about 4.0 to 7.0 and preferably between about 5.0 and 5.75 before and after the precipitation reaction, and be otherwise compatible in the oral environment. The ions must not combine prematurely in the solution to form a precipitate, but must be able to diffuse through the surface of the tooth to a demineralized subsurface area and be able to form an insoluble salt with ions of the other solution.

The solutions and the insoluble precipitates must have acceptable levels of toxicity (i.e., the particular ions, in the amounts used in the remineralization process, must be non-toxic).

In a preferred embodiment of the invention the demineralizing composition is a stable, one-part dry-mix. Such dry-mix contains from about 1.0% to 80.0% of at least one calcium salt, from about 1.0% to 80.0% of at least one phosphate salt, from about 0.1% to 20.0% of at least one water-soluble divalent metal salt wherein the metal in other than calcium, from about 0.1% to 20.0% of flavor, from about 0.1% to 30.0% of sweetener, from 0 to about 10.0% of a fluoride salt, and from 0 to about 5.0% of surfactant. The flavor is preferably provided as a spray dried powder.

In another preferred embodiment of the present invention, the remineralizing cationic phase of a dentifrice composition contains about 0.05% to 15.0%, preferably about 0.10% to 10%, of at least one soluble calcium salt yielding calcium ions and greater than about 0.001%, preferably from 0.001% to 2.0%, most preferably from about 0.01% to 1.0%, of at least one water-soluble divalent metal salt selected from the group consisting of magnesium, strontium, tin and zinc, with magnesium being preferred. The remineralizing anionic phase contains from about 0.05% to 15.0%, preferably about 0.10% to 10.0%, of dissolved phosphate salt yielding phosphate ions and from about 0.01% to 5.0%, preferably from about 0.02% to 2.0%, of a soluble fluoride salt yielding fluoride ions.

The resulting precipitate is a calcium phosphate or hydroxyapatite, the natural constituent of tooth enamel, with incorporated fluoride ions. Not only does this improved process result in remineralized enamel, but the remineralized enamel may be more resistant to subsequent demineralization than was the original enamel.

As the calcium compound it is, in principle, possible to employ, in the preparations of the invention, any water-soluble toxicologically harmless calcium compound. A compound is considered to be water-soluble when at least 0.25 gram thereof dissolves in 100 ml of $H_2O$ at 20° C.

Suitable water-soluble calcium compounds are, for example, calcium chloride, calcium bromide, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, or mixtures of water-soluble calcium compounds. Calcium nitrate is preferred. In the compositions of the invention for the remineralization of human dental enamel, at least about 100 ppm and perferably at least about 1000 ppm of calcium ions should be present; the upper limit is about 35,000 ppm of calcium ions.

Suitable water-soluble inorganic phosphates within the scope of the present invention are, for example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate. The concentration of the phosphate ions is at least about 100 ppm, and preferably at least about 1000 ppm to 40,000 ppm. Solubility in water is defined as in the case of the calcium compounds.

If desired, water-soluble salts yielding both calcium and phosphate ions, such as monobasic-calcium orthophosphate, may be employed.

As the stabilizing divalent metal compound it is also, in principle, possible to employ any water-soluble, non-toxic divalent metal compound which will stabilize the calcium and phosphate ions so that they do not rapidly or prematurely precipitate before diffusing into the teeth. In practice, however, it has been found that at least one member selected from the group consisting of magnesium, strontium, tin, and zinc, with magnesium being preferred, are the most effective in stabilizing the system.

Suitable magnesium compounds are, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds are, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds are, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds are, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

The concentration of divalent metal ions is at least about 10 ppm, and preferably at least about 100 ppm, with about 20,000 ppm or more being the upper limit. Solubility in water is, again, as defined as in the case of calcium and phosphate compounds.

The compositions of the invention for the remineralization or prevention of demineralization of human teeth may also contain water-soluble fluoride compounds, the caries-prophylactic activity of which has for a long time been considered to be established. When two phase systems are employed these compounds are preferably present in the phase containing phosphate in order to avoid the formation of sparingly soluble calcium fluoride.

Suitable fluoride compounds are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites.

Organic fluorides, such as the known amine fluorides are also suitable for use in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition other water-soluble monofluorophosphate salts may be employed including ammonium monofluorophosphate aluminum monofluorophosphate, and the like. If monofluorophosphate salts are used as the fluoride source in two component systems, they could be present in the first component along with the calcium cations without departing from the present invention. However, this is less desirable due to the potential loss of fluoride.

Suitable toothpastes and gels can be made by employing, in addition to the remineralizing agents of the invention, from about 0.5% to 65%, preferably from about 5% to 40%, of an abrasive, from about 0.2% to 5% of a sudsing agent, from about 0.1% to 5% of a binding agent, from 0% to 50% of a humectant, and the balance, water and minors. From about 1.0% to 10.0% of an inorganic thickener such as hydrated silica may be added.

In the case of two separate components, the pH of a component of such toothpaste or gel comprised of the active cationic or anionic ingredients each has a pH of more than about 3. The mixture of the two portions which is placed in the mouth, however, must have a pH between about 4.0 and 7.0 and, preferably, between about 5.0 and 5.75. The pH's of the cationic portion and the anionic portion can be adjusted so long as the above pH parameters are not exceeded.

Suitable abrasives include silica xerogels. Other conventional toothpaste abrasives can be used in the compositions of this invention, and include beta-phase calcium pyrophosphate, dicalcium phosphate dihydrate, anhydrous calcium phosphate, calcium carbonate, zironium silicate, and thermosetting polymerized resins. Silica aerogels and the insoluble metaphosphates such as insoluble sodium metaphosphate can be used. Mixtures of abrasives can be also be used. Silica xerogel abrasives are preferred.

Suitable sudsing agents are those which are reasonably stable and form suds throughout the period of application. Preferably, non-soap anionic or nonionic organic synthetic detergents are employed. Examples of such agents are water-soluble salts of alkyl sulfate having from 10 to 18 carbon atoms in the alkyl radical, such as sodium lauryl sulfate, water-soluble salts of sulfonated monoglycerides of fatty acids having from 10 to 18 carbon atoms, such as sodium monoglyceride sulfonate, salts of $C_{10}$–$C_{18}$ fatty acid amides of taurine, such as sodium N-methyl taurate, salts of $C_{10}$–$C_{18}$ fatty acid esters of isethionic acid, and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material is added to thicken and provide a desirable consistency for the present compositions. Suitable thickening agents are water-soluble salts of cellulose ethers, such as sodium carboxymethyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum.

It is also desirable to include some humectant material in a toothpaste or gel to keep it from hardening. Suitable humectants include glycerine, sorbitol, polyethylene glycol, propylene glycol, and other edible polyhydric alcohols as well as mixtures thereof.

Toothpaste or gel compositions may also contain flavoring agents such as oil of wintergreen, oil of peppermint, oil of spearmint, oil of sassafras, and oil of clove. Toothpaste or gel compositions may also contain sweetening agents such as saccharin, dextrose, levulose, sodium cyclamate, and aspartame Mixtures of sugar with a sweetner, e.g., sucralose, are contemplated.

It is also possible to manufacture the dentifrice product in the form of a transparent or transluent gel. This is accomplished by matching the refractive index of the water-humectant system with the abrasives and inorganic thickeners if used.

Professional gels can be formulated similar to dentifrices but with higher fluoride contents. Since these products are not designed for cleaning but only as a fluoride application, abrasives and other cleaning agents need not be included in the formulation.

The remineralizing systems herein can also be provided in the form of a mouthwash product. Both the cationic and anionic parts of mouthwashes can be made in accordance with the following. Mouthwashes generally comprise an aqueous solution of ethyl alcohol and flavoring materials. The alcohol provides an antibacterial effect, solubilizes the flavoring materials and provides a pleasant mouth feeling. Alcohol-free mouthwashes are now, however, gaining in popularity. Optionally, mouthwashes also contain additional antibacterial agents and humectants such as glycerine and sorbitol which give a moist feeling to the mouth.

In addition to the remineralizing agents of the invention, typical mouthwashes contain about 0 to 30%, preferably about 0 to 20%, ethyl alcohol; about 30% to 90% water; about 0 to 20% glycerine or other humectant; about 0 to 0.1% of an antibacterial agent; about 0 to 0.2% of a soluble fluoride source, about 0.01% to 0.5% of a sweetening agent, about 0.01% to 2.0% of a flavoring agent, and from about 0.1% to 1% of an emulsifier-surfactant.

Examples of suitable flavoring agents include heliotropyl nitrile, wintergreen oil (methyl salicylate), oil of peppermint, oil of assia, oil of anise, oil of cinnamon, and mixtures thereof. Suitable sweetening agents include saccharin, glycerine, sorbitol, levulose, and 6-(trifluoromethyl)-tryptophane and aspartyl phenylalanine methyl ester.

The products of the present invention can be prepared as single solutions, as two separate solutions, in a single solid powdered, gel for paste form, or a solid powder, gel or paste comprised of two separate components.

In accordance with this invention a single solution comprised of the ingredients set forth below is prepared as follows. The product is prepared by dissolving at least one water-soluble calcium salt in a concentration of from 0.05% to 15.0%. At least one water-soluble divalent metal salt, other than a calcium salt, is added in a concentration greater than about 0.001% and preferably from about 0.001% to 2.0%. A second solution containing at least one water-soluble phosphate salt at a concentration of from about 0.05% to 15.0% is also prepared. If desired, at least one water-soluble fluoride releasing compound may be added to the phosphate containing solution at a concentration of from about 0.01% to 5.0%. The pH of each solution is adjusted so that upon mixing the final total solution pH will be between about 4.0 and 7.0, preferably between about 5.0 to 5.75. The two solutions are then mixed to produce a stable supersaturated or nearly supersaturated solution of calcium phosphate. In this preferred embodiment of the invention it is preferable to use sodium monofluorophosphate as the fluoride source. This keeps the fluoride in solution even in the presence of high concentrations of calcium and allows the supersaturated calcium phosphate solutions to remain stable for longer periods.

When the total concentration of calcium ions and phosphate ions is such that the mixing results in a metastable solution, i.e., one that eventually precipitations calcium phosphate on standing, the two solutions are kept separately until it is desired to use the admixed product and obtain the advantage of the stabilizing divalent metal ions of the present invention.

In another embodiment of this invention there is provided a product for remineralizing dental enamel comprising: (i) a first component comprising from about 0.05% to 15.0%, preferably about 0.10% to 10%, of at least one water-soluble calcium salt together with from about 0.001% to 2.0%, preferably about 0.01% to 1.0% of at least one water-soluble, non-toxic divalent metal salt other than a calcium salt; (ii) a second component comprising from about 0.05% to 15.0%, preferably about 0.10% to 10% of at least one water-soluble phosphate salt, and if desired, from about 0.01% to 5.0% and, preferably from about 0.02% to 2.0% of at least one fluoride releasing agent, (iii) a dispensing container comprising at least two discreet compartments each with an outlet end, the first compartment storing the first component which includes soluble calcium salt together with soluble divalent metal salt and the second compartment storing the second component which includes soluble phosphate salt and, if desired, together with the fluoride source, (iv) a closure mechanism for closing the compartments; and (v) wherein when the two components are mixed the pH in between about 4.5 and 7.0 and preferably between about 5.0 and 5.75.

A plurality of packaging methods may be employed in order to separately contain or store the two components and provide effective dispensing thereof into the oral cavity.

Thus, the two components of a toothpaste, gel, cream, or the like, may be simultaneously dispensed from separate collapsible tubes preferably made of plastic, a plastic and metal laminate, etc. For convenience and in order to aid in dispensing substantially equal amounts of the components, the tubes may be held together by banding or cementing, preferably along the corresponding ventral sides of the tubes.

In another embodiment the two tubes may be constructed to have abutting, preferably flat, sidewall portions. In the forgoing embodiments the mouths of the tubes are usually sufficiently close so that sufficient quantities of the components of the toothpaste or gel may be simultaneously dispensed directly on the toothbrush with the tubes the being capped separately.

Alternatively, another packaging method comprises loading each component of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and aniomic components, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of outer tube and the mouth of the inner tube. The closures of this tube-within-a-tube, (which can screw on the outer tube or simply be held by pressure), may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement comprises of a pressurized container which is provided with two compartments and two spouts. The internal pressure of the compartments is maintained by a pressurized gas, i.e., nitrogen, at the bottom of each compartment. Operation of a mechanical actuator actuates valves which release the contents of the compartments through the spouts causing discharge of the paste or gel components onto a brush.

The mouthwash or rinse and similar liquid embodiments are maintained in a manner similar to the pastes or gels in that during storage, each of the components are maintained separate from one another to prevent premature reaction. Upon dispensing, the components mix and react in the oral cavity to effect remineralization of dental enamel. The liquid components can therefore be stored each in separate compartments of a dual-compartment dispenser. The dispenser usually includes a closure system comprising for example, an inclined crown portion, at least two pouring spouts extending upwardly from an upper surface of the crown portion and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve as a window function for gauging the amounts of liquid remaining in the dispenser. The walls of the containers can be described or otherwise calibrated to assist in dispensing the correct remineralizing amount of product.

While applicants do not wish the scope of the present invention to be limited by theory, it is believed that the calcium, phosphate, and, optionally, the fluoride ions diffuse through the tooth surface to the demineralized subsurface and precipitate in the demineralized subsurface where they remineralize the tooth structure. This is attainable because sufficient calcium, phosphate, and fluoride ions remain soluble for a period of time sufficient to permit their diffusion into the demineralized subsurface of the dental enamel. This is accomplished by the use of the divalent metal cations of this invention and in the instance of two component systems combining the particular ions just prior to their application to the tooth in a solution having a pH of about 4.0 to 7.0 and preferably from about 5.0 to 5.75 at which pH enough of the calcium, phosphate, and fluoride ions remain soluble for the period of time required to remineralize the lesions of the dental enamel.

Chemically equivalent concentrations of the first and second solutions are not necessary as long as the molar ratio of calcium and phosphate ions in the mixture is from about 0.01 to up to 100 to 1. It is preferred that the ratio is from about 0.2 to 1 to 5 to 1, and it is most preferred that the ratio is from about 1:1 to 1.67 to 1, the ratio of calcium to phosphate in the range of the various less soluble calcium phosphate salts.

While completely aqueous solutions are preferred in the present invention, non-aqueous solvents may be employed in combination with water. For example, suitable nonaqueous solvents include ethyl alcohol, glycerine and propylene glycol. Solvent systems suitable for use in the present invention are those which are capable of dissolving the salts employed in the invention and which are safe for use in the mouth.

With regard to the period of time of exposure of the solutions to the teeth, it is necessary that the length of time be great enough to allow diffusion of the ions into the demineralized subsurface. At least about ten seconds are required for this diffusion. The solution is preferably applied to the teeth for from about 10 seconds to about 15 minutes. The pH of the solution remains relatively constant after its introduction into the oral cavity. Under some conditions calcium phosphate readily precipitates at this pH, but most surprisingly while some of the precipitation may occur immediately and some small amount even before application to the teeth, substantially greater amounts of calcium, phosphate and fluoride ions remain in solution to diffuse into the teeth and remineralize the demineralized dental enamel due to the presence of the divalent metal cations hereinbefore described. It is believed that the ability of the solutions to provide ions for remineralization is greatest upon their first introduction into the oral cavity, thereafter decreasing, but at a rate less than that encountered when not employing the instant divalent metal cations.

When using two component systems the time period between the mixing of the first and second solutions and the application of the mixture to the teeth should not exceed 1 minute, and preferably is less than 1 minute. With a toothpaste, gel, and the like, mixing is achieved on the surface to the teeth while brushing. The essence of the present invention lies in the mixing of components and the quick and timely application of the resulting solution which will precipitate calcium phosphate, calcium fluoride, and calcium fluoro-apatite in the subsurface enamel of the teeth. Before such precipitation occurs, the mixture comprising the solution must quickly be applied to the teeth. Surprisingly, the solution can have a pH of about 4.0 to 7.0, but preferably about 5.0 to 5.75 to achieve this result. At a pH below about 3, demineralization occurs rapidly. A pH below 2.5 is generally undesirable from a safety standpoint.

The pH of the solutions of the present invention may be adjusted to the pH desired by methods well known in the art. The pH may be lowered by the addition of any acid which is safe for use in the oral cavity and which yields the desired pH at the amount employed. Examples of suitable acids are acetic acid, phosphoric acid, hydrochloric acid, citric acid and malic acid.

The following Examples illustrate the invention: In the Examples and elsewhere herein parts and percent are by weight unless otherwise stated.

EXAMPLES 1–3

Artificial lesions, about 50 u deep, were formed in one surface of bovine enamel chips using a demineralizing Carbopol gel, which was used to treat the specimens for 72 hours. The surface hardness of the surface to be treated was then measured.

The regimen cycle consisted of a 30 minute demineralization in a standard demineralizing solution followed by a 5 minute treatment of the test products diluted 1 part product to two parts human saliva, followed by a 60 minute remineralization in human saliva. Overnight, which was every fifth cycle, the specimens were kept with a layer of saliva and stored in a cold room. The test ran for three days, from a total of 15 demineralization:treatment:remineralization cycles.

For the treatment cycle, the two parts of the remineralizing test agents of the example were separately diluted 1 part product to 2 parts saliva and mixed together immediately before immersion of the enamel specimens.

The two part oral remineralizing treatment was prepared as follows:

sodium monofluorophosphate is generally less effective at promoting remineralization than sodium fluoride.

EXAMPLE 4

The following formulations were prepared:

|  | Example 4 | | Control B* | |
|---|---|---|---|---|
|  | Part A | Part B | Part A | Part B |
| Calcium nitrate | 3.0 | 0.0 | 0.0 | 0.0 |
| Magnesium chloride | 0.8 | 0.0 | 0.0 | 0.0 |
| Monopotassium phosphate | 0.0 | 0.6 | 0.0 | 0.0 |
| Dipotassium phosphate | 0.0 | 2.1 | 0.0 | 0.0 |
| Glycerine | 24.0 | 22.85 | 50.0 | 50.0 |
| Water | 72.2 | 74.45 | 50.0 | 50.0 |

*The pH of the control was adjusted to 5.5.

A similar treatment regimen was performed as for Examples 1–3 except that in Test 1 the treatment time was 15 minutes using the formulation of Example 4. In Test II, and Control Test III the first cycle of the day was a 5 minute treatment with Crest and cycles 2, 3, 4, and 5 were a 15 minute treatment with the formulation of Example 4 or Control B respectively. The 15 minute treatment time was chosen to replicate what might happen if this formulation was released from a produce where the treatment time might be extended to 15 minutes. The three tests were also compared with a standard Crest treatment in which Crest treatment was applied 5 times per day for 5 minutes. The test was run for 3 days for a total of 15 cycles.

|  | Test I | Test II | Control Test III | Crest |
|---|---|---|---|---|
|  | Example 4 5 cycles/day | Example 4 4 cycles/day Crest 1 cycle/day | Control B 4 cycles/day Crest 1 cycle/day | 5 cycles/day |
| Hardness increase | 10.0 | 13 | 6.0 | 16 |

The results show that treatments with the non-fluoride containing remineralizing formulation was effective in rem-

|  | Control A | | Example 1 | | Example 2 | | Example 3 | |
|---|---|---|---|---|---|---|---|---|
|  | Part A | Part B | Part A | Part B | Part A | Part B | Part A | Part B |
| Calcium nitrate | 3.00 | 0.00 | 3.0 | 0.00 | 3.0 | 0.00 | 3.00 | 0.00 |
| Magnesium chloride | 0.00 | 0.00 | 0.4 | 0.00 | 0.8 | 0.00 | 0.8 | 0.00 |
| Monopotassium phosphate | 0.00 | 2.00 | 0.0 | 2.10 | 0.0 | 2.10 | 0.0 | 2.40 |
| Dipotassium phosphate | 0.00 | 0.0 | 0.0 | 0.60 | 0.0 | 0.60 | 0.2 | 0.20 |
| Sodium fluoride | 0.00 | 0.50 | 0.0 | 0.50 | 0.0 | 0.50 | 0.0 | 0.00 |
| Sodium MFP | 0.00 | 0.00 | 0.0 | 0.00 | 0.0 | 0.00 | 0.0 | 1.80 |
| Glycerine | 24.00 | 22.85 | 24.0 | 22.85 | 24.0 | 22.85 | 24.0 | 22.85 |
| Water | 73.00 | 73.95 | 72.6 | 73.95 | 72.2 | 73.95 | 72.2 | 72.75 |

The pH of each after mixing the two parts was approximately 5.5.

|  | Crest | Control A | Example 1 | Example 2 | Example 3 |
|---|---|---|---|---|---|
| Hardness increase | 16 | 20.0 | 62 | 49.0 | 21.0 |

The results show that Examples 1 and 2 containing sodium fluoride and magnesium chloride significantly outperform Control A and Crest which do not contain magnesium chloride. Example 3 containing sodium monofluorophosphate and magnesium chloride performed equal to Control A and better than Crest. This is surprising since ineralizing teeth. Test I illustrates it was slightly less effective on a one to one treatment basis with Crest. However, Test II compared to Control Test III illustrates it was more effective than Crest on a five to one treatment basis than Crest. When used with the fluoride toothpaste the remineralizing treatments had an additive remineralizing effect. This demonstrates the likely positive effects of a non-fluoride product, i.e., a lozenge or candy containing the remineralizing ingredients if repeated several times a day e.g. after eating.

EXAMPLES 5–7

Examples 5–7 illustrate various embodiments of remineralizing formulation of the invention. A two part oral remineralizing mouthwash and a two part remineralizing toothpaste and a one phase toothpaste are prepared as follows.

|  | Example 5 Mouthrinse | | Example 6 Toothpaste | | Example 7 |
|---|---|---|---|---|---|
|  | A | B | A | B | Toothpaste |
| Water | 73.8 | 75.9 | 21.7 | 21.5 | 0.0 |
| Sorbitol |  |  | 40.0 | 40.0 | 0.0 |
| Glycerine | 20.0 | 20.0 | 10.0 | 10.0 | 69.66 |
| Silica abrasive |  |  | 15.0 | 15.0 | 12.0 |
| Silica thickener |  |  | 6.0 | 6.0 | 4.0 |
| CMC |  |  | 1.0 | 1.0 | 0.0 |
| Carbowax 8000 |  |  |  |  | 5.0 |
| Sodium lauryl sulfate |  |  | 1.5 | 1.5 | 1.5 |
| Calcium nitrate tetrahydrate | 4.5 | 0.0 | 3.0 | 0.0 |  |
| Calcium chloride anhydrous |  |  |  |  | 3.0 |
| Dipotassium phosphate |  | 0.5 |  | 0.2 | 0.0 |
| Monopotassium phosphate |  | 3.0 |  | 2.3 | 3.0 |
| Magnesium chloride hexahydrate | 1.2 | 0.0 | 0.8 | 0.0 |  |
| Magnesium oxide |  |  |  |  | 0.4 |
| Sodium monofluorophosphate | 0.0 | 0.0 |  | 1.5 | 0.0 |
| Sodium fluoride |  | 0.1 |  |  | 0.24 |
| Flavor | 0.4 | 0.4 | 0.8 | 0.8 | 0.9 |
| Saccharin | 0.1 | 0.1 | 0.2 | 0.2 | 0.3 |

EXAMPLES 8–10

To further demonstrate the beneficial effects of magnesium, strontium, zinc and stannous ions in stabilizing supersaturated solutions of calcium phosphate, the following examples and controls were prepared.

|  | Example 8 | Example 9 | Example 10 | Control C |
|---|---|---|---|---|
|  | Part A | Part A | Part A | Part A |
| Calcium nitrate | 1.44 | 1.44 | 1.44 | 1.44 |
| Zinc chloride | 0.015 | 0.00 | 0.00 | 0.00 |
| Stannous chloride | 0.00 | 0.01 | 0.00 | 0.00 |
| Strontium chloride | 0.00 | 0.00 | 0.30 | 0.00 |
| Water | 73.545 | 73.55 | 73.26 | 73.56 |
|  | Part B | Part B | Part B | Part B |
| Monopotassium phosphate | 0.37 | 0.42 | 0.42 | 0.42 |
| Dipotassium phosphate | 0.14 | 0.07 | 0.07 | 0.07 |
| Water | 74.49 | 74.51 | 74.51 | 74.51 |

The two parts of each example were mixed and the time taken for the solutions to become cloudy was measured with the following results.

|  | After Mixing | | | |
|---|---|---|---|---|
| pH Start | 5.6 | 5.45 | 5.54 | 5.60 |
| Minutes before becoming cloudy | 10 | 10 | 9 | 6 |

The results show that the three examples of the invention remained stable for longer than the control product which did not contain a divalent metal salt. The addition of the divalent metal thus allows more time for penetration into the tooth before precipitation occurs.

EXAMPLES 11–12

The following monofluorophosphate-containing examples were prepared:

|  | Example 11 | Example 12 | Control |
|---|---|---|---|
|  | Part A | Part A | Part A |
| Calcium nitrate | 1.28 | 2.01 | 1.28 |
| Magnesium chloride | 0.10 | 0.01 | 0.00 |
| Stannous chloride | 0.00 | 0.01 | 0.00 |
| Water | 73.545 | 73.55 | 73.72 |
|  | Part B | Part B | Part B |
| Monopotassium phosphate | 0.91 | 1.02 | 0.91 |
| Dipotassium phosphate | 0.12 | 0.08 | 0.12 |
| Sodium monofluorophosphate | 0.43 | 0.43 | 0.43 |
| Water | 74.49 | 73.47 | 73.55 |
| pH Start | 5.64 | 5.45 | 5.69 |
| Minutes before becoming cloudy | 7.5 | 10 | 2.5 |

The magnesium chloride and stannous chloride, stabilized the solutions from early precipitation of calcium phosphate even in the presence of MFP as shown by the longer times before the solutions became cloudy.

The above examples show how divalent metals of the invention sucessfully retard the precipitation of calcium phosphates.

EXAMPLES 13–15

Examples of suitable mouthwashes and toothpastes are shown below in Examples 13–15.

|  | Example 13 Professional Gel | | Example 14 Mouthwash | | Example 15 |
|---|---|---|---|---|---|
|  | Part A | Part B | Part A | Part B | Toothpaste |
| Water | 28.3 | 30.9 | 73.6 | 75.8 |  |
| Glycerine | 10.0 | 10.0 | 10.0 | 10.0 | 64.06 |
| Sorbitol | 40.0 | 40.0 | 10.0 | 10.0 |  |
| Silica abrasive |  |  |  |  | 15.0 |
| Silica thickener | 12.0 | 12.0 |  |  | 5.0 |
| Xanthan gum | 0.9 | 0.9 |  |  |  |
| Sodium lauryl sulfate |  |  |  |  | 1.5 |
| Calcium nitrate | 7.5 | 0.0 | 5.5 | 0 | 5.0 |
| Stannous chloride | 0.1 | 0.0 |  |  |  |
| Zinc chloride |  |  | 0.1 | 0 |  |
| Strontium chloride |  |  |  |  | 0.2 |
| Dipot. Phosphate | 0.0 | 0.2 | 0 | 0.2 | 0.3 |
| Monopot. Phosphate | 0.0 | 4.2 | 0 | 3.2 | 3.2 |
| Sodium MFP |  |  |  |  | 0.76 |
| Sodium fluoride | 0.0 | 1.0 |  |  |  |
| Flavor | 0.5 | 0.5 | 0.5 | 0.5 | 0.7 |
| Saccharin | 0.3 | 0.3 | 0.3 | 0.3 | 0.4 |
| Carbowax 8000 |  |  |  |  | 2.0 |

EXAMPLES 16–17

Examples 16–17 illustrate dry-mix formulations which are employed when added to and mixed with water.

|  | Example 16 |
| --- | --- |
| Calcium gluconate | 65.0 |
| Magnesium chloride | 10.0 |
| Monosodium phosphate | 12.5 |
| Disodium phosphate | 2.5 |
| Stannous fluoride | 2.5 |
| Flavor | 5.0 |
| Saccharin | 2.5 |
| Usage Concentration | 1.2 g per oz |

Example 17 illustrates dry-mix for us as an effervescent mouthwash.

|  | Example 17 |
| --- | --- |
| Encapsulated* calcium nitrate 97% | 36.0 |
| Monopotassium phosphate | 30.0 |
| Malic acid | 11.0 |
| Magnesium chloride | 5.0 |
| Sodium bicarbonate | 10.0 |
| Sodium fluoride | 2.0 |
| Flavor | 4.0 |
| Saccharin | 2.0 |
| Usage Concentration | 5.0 g per oz |

*Calcium nitrate encapsulated with water soluble ethyl cellulose encapsulent

What is claimed is:

1. An aqueous product for remineralizing subsurface lesions in teeth consisting essentially:
   (i) from about 0.05% to 15.0% by weight of at least one water-soluble calcium salt;
   (ii) at least about 0.001% by weight of at least one water-soluble, non-toxic divalent metal salt wherein the divalent metal is other than calcium, further wherein the divalent metal salt is selected from the group consisting of divalent metal acetate, divalent metal ammonium sulfate, divalent metal benzoate, divalent metal bromide, divalent metal borate, divalent metal citrate, divalent metal chloride, divalent metal gluconate, divalent metal hydroxide, divalent metal iodide, divalent metal oxide, divalent metal propionate, divalent metal D-lactate, divalent metal DL-lactate, divalent metal phenolsulfate, divalent metal sulfate, divalent metal nitrate, and divalent metal nitrate;
   (iii) from about 0.05% to 15.0% by weight of at least one water-soluble orthophosphate salt;
   (iv) from 0% to 5.0% by weight of at least one water-soluble fluoride salt;
   (v) from about 100 ppm to about 35,000 ppm of dissolved calcium ions released by the calcium salt;
   (vi) from about 10 ppm to about 20,000 ppm of dissolved divalent metal ions released by the divalent metal salt;
   (vii) from about 100 ppm to about 40,000 ppm of dissolved orthophosphate ions released by the orthophosphate salt; and
   (viii) from 0 ppm to about 5000 ppm of dissolved fluoride ions released by the fluoride salt;
   wherein the product has a pH of from about 5.0 to 5.75.

2. The product according to claim 1 comprising from about 0.10% to 10.0% by weight of said at least one calcium salt.

3. The product according to claim 1 comprising from about 0.001% to 2.0% by weight of said at least one divalent metal salt.

4. The product according to claim 1 wherein the divalent metal is selected from the group consisting of magnesium, strontium, tin, and zinc.

5. The product according to claim 1 wherein the orthophosphate salt content is from about 0.10% to 10.0% of said orthophosphate salt.

6. The product of claim 1 further comprising from about 0.01% to 5.0% by weight of the at least one water-soluble fluoride salt which yields fluoride ions.

7. The product according to claim 6 comprising from about 0.02% to 2.0% by weight of said at least one fluoride salt.

8. The product according to claim 1 wherein the molar ratio of said released calcium ions to said released phosphate ions is from about 0.01 to 1 up to 100.0 to 1.

9. The product according to claim 8 wherein the molar ratio of said released calcium ions to said released phosphate ions is from about 0.2 to 1 up to 5.0 to 1.

10. The product according to claim 1 wherein the product is a paste, a gel or a professional gel.

11. The product according to claim 1 wherein the product is a liquid mouthwash or rinse.

12. The product according to claim 1 wherein the product contains from about 20 ppm to 5,000 ppm of the fluoride ions.

13. The product according to claim 1 wherein the product has a pH of about 5.5.

14. The product according to claim 1 wherein the water-soluble calcium salt is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, and mixtures thereof.

15. The product according to claim 1 wherein the water-soluble calcium salt is selected from the group consisting of calcium chloride, calcium bromide and calcium nitrate.

16. The product according to claim 1 wherein the water-soluble calcium salt is calcium nitrate.

* * * * *